(12) United States Patent
Yu

(10) Patent No.: US 7,404,402 B2
(45) Date of Patent: Jul. 29, 2008

(54) WHIPLASH RESTRAINER

(75) Inventor: Chun Ho Yu, Hong Kong (HK)

(73) Assignee: M & B Innovations Limited, Hong Kong (HK)

( * ) Notice: Subject to any disclaimer, the term of this patent is extended or adjusted under 35 U.S.C. 154(b) by 268 days.

(21) Appl. No.: 11/374,925

(22) Filed: Mar. 13, 2006

(65) Prior Publication Data

US 2007/0209667 A1     Sep. 13, 2007

(51) Int. Cl.
*A61F 11/00* (2006.01)
(52) U.S. Cl. .............................. 128/857; 297/464; 2/410
(58) Field of Classification Search ................ 128/587; 27/216.12; 244/122; 2/2.14, 410
See application file for complete search history.

(56) References Cited

U.S. PATENT DOCUMENTS

| 3,698,670 | A | * | 10/1972 | Ewing ................... 244/122 AG |
| 3,873,996 | A | | 4/1975 | Varteressian |
| 3,922,034 | A | | 11/1975 | Eggert |
| 4,592,523 | A | * | 6/1986 | Herndon ................ 244/122 AG |
| 4,664,341 | A | * | 5/1987 | Cummings ............ 244/122 AG |
| 4,909,459 | A | | 3/1990 | Patterson |
| 4,967,985 | A | * | 11/1990 | Deakin ................. 244/122 AG |
| 6,009,566 | A | | 1/2000 | Hubbard |
| 6,363,540 | B1 | | 4/2002 | Myers |
| 6,572,137 | B2 | * | 6/2003 | Bossecker et al. ......... 280/730.1 |
| 6,619,751 | B1 | * | 9/2003 | Shah .......................... 297/464 |
| 6,623,075 | B2 | * | 9/2003 | Baloga et al. ............. 297/250.1 |
| 6,709,062 | B2 | * | 3/2004 | Shah .......................... 297/464 |
| 6,931,669 | B2 | * | 8/2005 | Ashline ......................... 2/422 |
| 2002/0043831 | A1 | * | 4/2002 | Alsup .................... 297/216.12 |
| 2005/0088030 | A1 | * | 4/2005 | Stoll .......................... 297/466 |

FOREIGN PATENT DOCUMENTS

DE         2330950 A1     1/1975

* cited by examiner

*Primary Examiner*—Terrell Mckinnon
*Assistant Examiner*—James M Robinson
(74) *Attorney, Agent, or Firm*—The Maxham Firm

(57) ABSTRACT

A whiplash restrainer for use by riders in vehicles, generally in conjunction with safety belts. A helmet-like device is secured, with reasonable freedom of motion of the rider's head, to a shock absorber by a joint device. The shock absorber is removeably secured to the vehicle seat back.

29 Claims, 10 Drawing Sheets

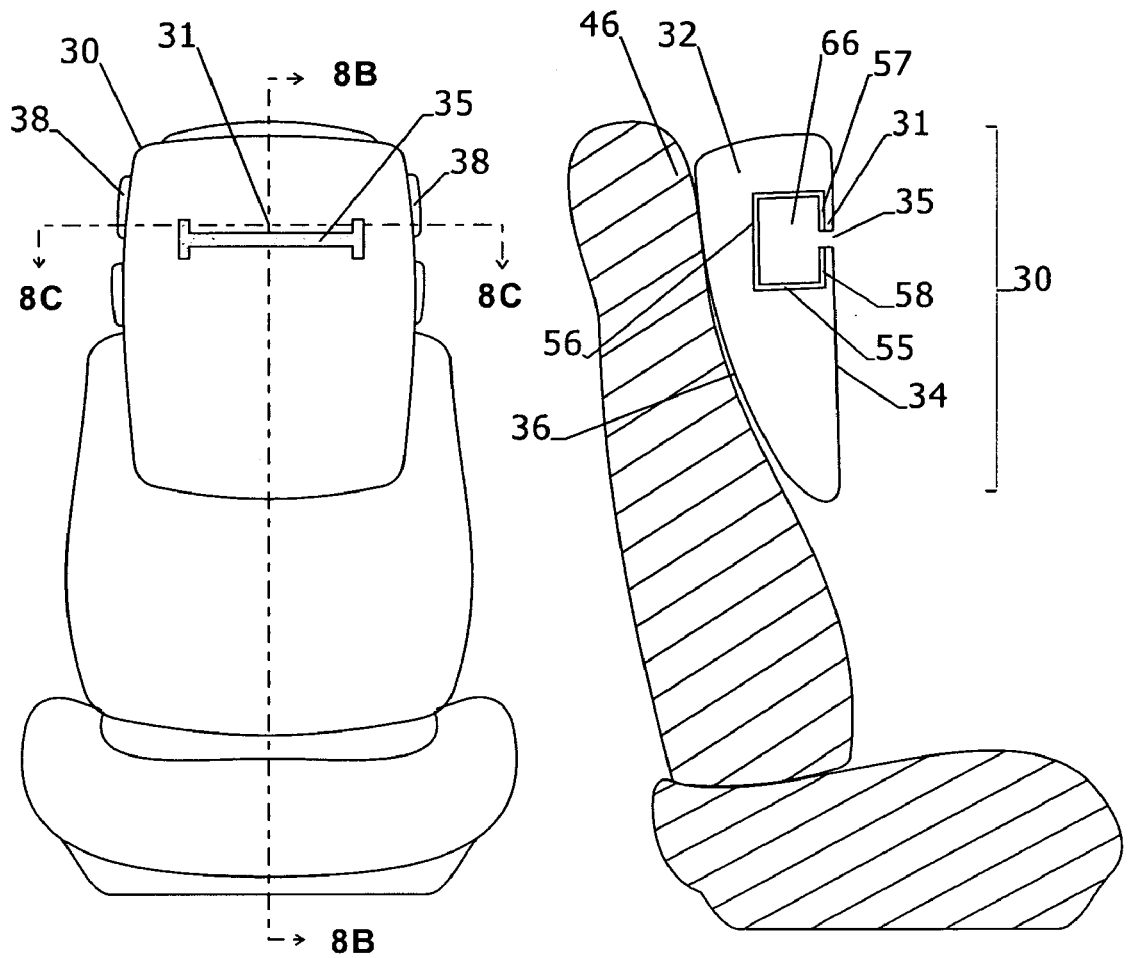
FIG.8A
FIG.8B
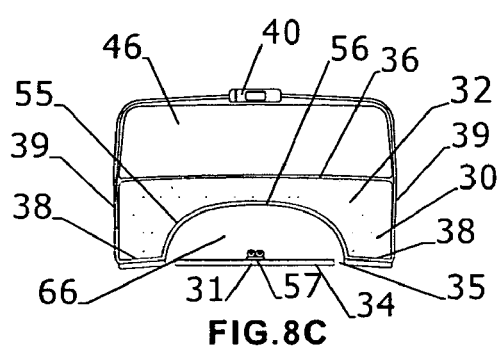
FIG.8C

WHIPLASH RESTRAINER

BACKGROUND

1. Field of Invention

This invention relates generally to a safety device for drivers and passengers of vehicles, such as automobiles, speedboats, aircrafts and the like, and is more particularly designed for preventing head or neck injury caused by sudden and dramatic change in speed, such as in traffic crashes.

2. Discussion of Related Arts

Although the use of safety belts has greatly reduced the number of injuries and deaths in traffic accidents, many drivers or passengers, generally referred to herein as "riders," still suffer from head or neck injuries in traffic accidents or sudden and dramatic changes in speed when using safety belts. The deficiency of the safety belt is that it only restrains that portion of the body part below the neck of the seat-belt user. The head of the user is still subject to large deceleration forces during a crash, which often results in head or neck damage to the user, commonly known as "whiplash."

Whiplash is a soft tissue (with or without bone) injury to the neck resulting in neck sprain or neck strain. Such injury is usually caused by the sudden backward movement (extension) and forward movement (flexion) of the neck during a vehicle crash when the rider's body experiences dramatic change in speed in a very short time interval. Severe whiplash may cause injury to intervertebral joints, discs, ligaments, cervical muscles and nerve roots, vertebral bone fracture, or may even be fatal to the rider.

During a crash or sudden change in speed, the head of the user is fixed safely on the headrest by the present invention, and the body part below the neck position of the user is fixed onto the seat by the seat belt. The continuing forward or backward movement of the head or the neck with respect to the body of the user is avoided by the present invention.

Prior art U.S. Pat. No. 6,363,540 discloses a helmet with the forehead portion of the helmet being connected to the seat by a strap. The disadvantage of this device is that during sudden deceleration, the restraint force is applied mainly to the forehead of the user, while the continuing forward motion of the head and neck, with the forehead being restrained, will result in hyper-extension, thereby causing neck injury. The strap also experiences high frictional force in the channel for its large contact surface area which hinders the turning movement of the user's head. The rigid shell design of the helmet is also inconvenient for a domestic car driver.

U.S. Pat. No. 4,909,459 discloses another restraint device. The disadvantage of this device is that a considerable length of the strap between the loop and the helmet is required to allow a free and smooth rotational movement of the user's head, while the increased length will fail to restrain the backward movement (extension) and forward movement (flexion) of the neck to prevent the whiplash.

Prior art U.S. Pat. No. 6,009,566 discloses another restraint device using a restraining yoke and collar. The disadvantage of this device is that it is inconvenient and uncomfortable for riders in domestic cars. The strap restrains the user's head movement in a horizontal plane and limits the rotational movement of the head. A considerable length of the strap is required to enable a free rotation of the user's head, while such increased length of the strap will reduce the protection against whiplash, as encountered in the '459 patent.

The existing safety restraints do not effectively restrain the backward movement (extension) and forward movement (flexion) of the neck so as to prevent whiplash. Some restraint devices are inconvenient and uncomfortable for the riders in domestic car. Other restraint devices either restrain the rotational movement of the user's head or otherwise limit the range of vision of the user.

SUMMARY OF THE INVENTION

A purpose of the present invention is to provide a whiplash restrainer to be used with a body restraining device to protect the user from whiplash.

Another object of the invention is to provide a whiplash restrainer which comprises a head and neck restrainer, a shock absorber and a joint device, the joint device being embedded in the shock absorber and connecting the head and neck restrainer with the shock absorber.

Another object of the present invention is to provide a whiplash restrainer which comprises a head and neck restrainer, a shock absorber and a joint device, the shock absorber confining the head and neck restrainer close to its front surface and preventing the neck of the user from bending up or down, except for a very limited degree.

Another object of the invention is to provide a whiplash restrainer which restrains the user's neck from moving forward or backward beyond the vertical axis of the body.

Still another object of this invention is to provide a whiplash restrainer which prevents any sudden extension or flexion on the neck of the user which may result in whiplash.

Yet another object of the present invention is to provide a whiplash restrainer containing a head and neck restrainer which is worn on the user's head and follows the movement of the head, providing forward and lateral fields of view for the user.

A further object of this invention is to provide a whiplash restrainer containing a head and neck restrainer and a joint device which enables the user's head to turn freely and smoothly in the horizontal plane.

Another object of the invention is to provide a whiplash restrainer containing a head and neck restrainer and a joint device which enables the user's head to rotate and move freely to a limited degree to prevent the type of backward and forward movement of the neck which results in whiplash.

Still another object of the present invention is to provide a whiplash restrainer containing a joint device which uses bearings to reduce the friction experienced at the joint during the turning movement of the user's head.

A further object of the invention is to provide a whiplash restrainer containing a joint device with a T-shaped rail to enhance the durability of the joint.

Yet another object of the invention is to provide a whiplash restrainer containing a shock absorber, the size of which can be readily adjusted to fit with the user's head and neck.

Another object of this invention is to provide a whiplash restrainer containing a shock absorber which absorbs the shock from behind when the vehicle collision occurs at the back, and prevents the shock from transmitting directly to the user.

Yet another object of this invention is to provide a whiplash restrainer which can be conveniently put on and removed from the user.

A still further object of the invention is to provide a whiplash restrainer which can be conveniently installed onto any existing vehicle seat.

BRIEF DESCRIPTION OF DRAWING

The above and other aspects, features, and advantages of the present invention will become more apparent upon consideration of the following detailed description of preferred embodiments, taken in conjunction with the accompanying drawing figures, wherein:

FIG. 8A is a front view of the shock absorber in accordance with an embodiment of the present invention;

FIG. 8B is a cross-sectional view of the shock absorber, taken along line 8B-8B of FIG. 8A;

FIG. 8C is a cross-sectional view of the shock absorber, taken along line 8C-8C of FIG. 8A;

DETAILED DESCRIPTION OF THE PREFERRED EMBODIMENTS

Figure 1:
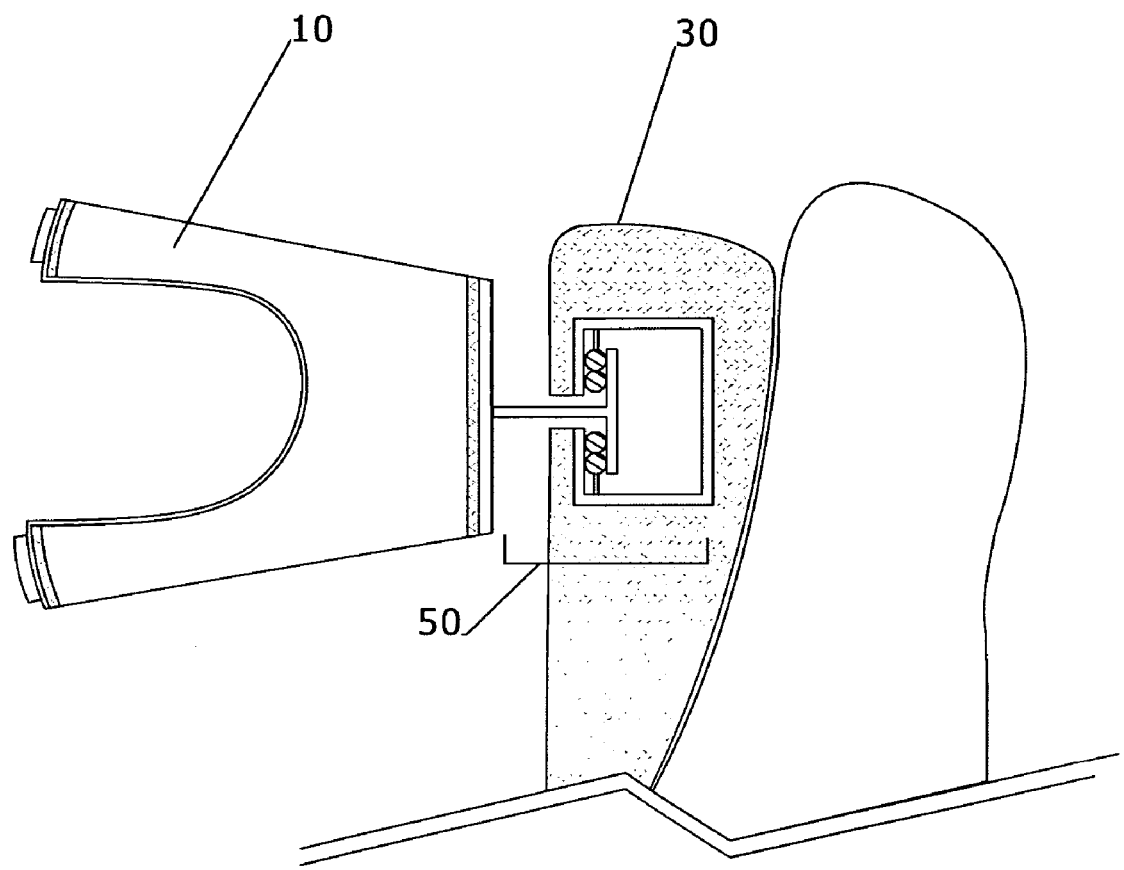
FIG. 1 is a stylized sectional view of a whiplash restrainer in accordance with an embodiment of the present invention.
Figure 2:
FIG. 2 is a perspective view of the whiplash restrainer in accordance with an embodiment of the present invention in use.

With reference now to the drawing, and more particularly to FIGS. 1 and 2, a preferred embodiment of the present invention is shown which includes head and neck restrainer 10, shock absorber 30, and joint device 50.

Figure 3A:
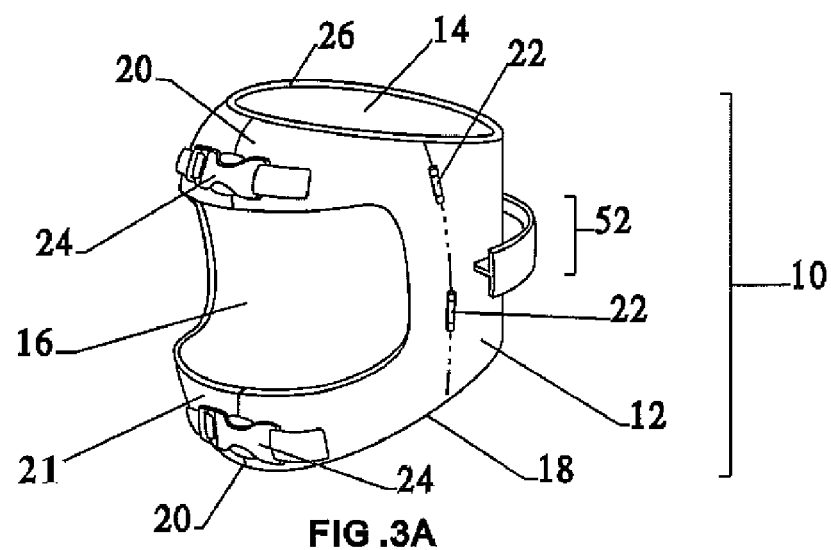
FIG. 3A is a perspective view of a head and neck restrainer portion of the apparatus of FIG. 2.
Figure 3B:
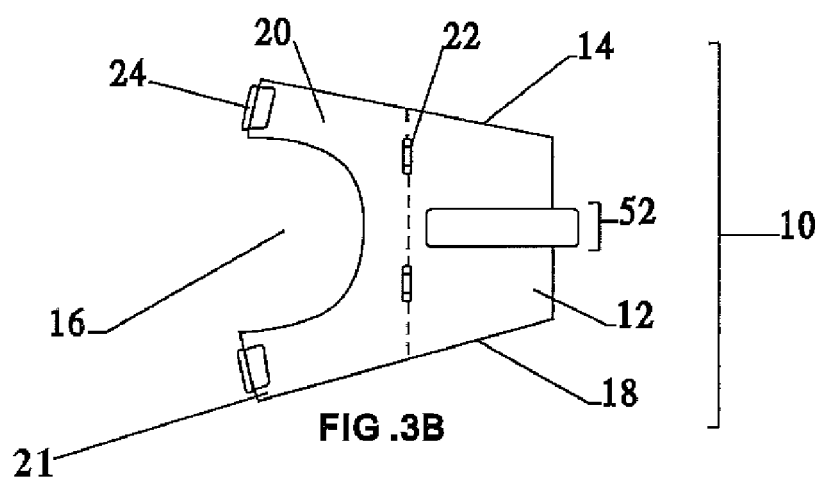
FIG. 3B is a side view of the head and neck restrainer of FIG. 3A.
Figure 3C:
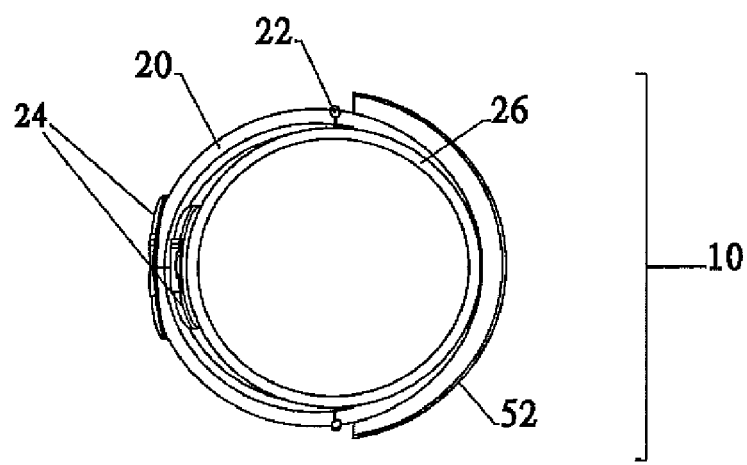
FIG. 3C is a top plan view of the head and neck restrainer of FIG. 3A.

As illustrated in FIGS. 3A, 3B and 3C, head and neck restrainer 10 has rigid outer shell 12 enclosing the forehead, the chin, the side and the back of the user's head. The head and neck restrainer has top opening 14, front opening 16 and bottom opening 18 exposing the corresponding areas of the user's head. The top opening and the front opening facilitate the ventilation inside the head and neck restrainer. The front opening also provides forward and lateral fields of view for the user. The outer shell is formed from a rigid material, such as aluminum.

Head and neck restrainer 10 is further provided with front portions 20 at the forehead area and the chin area of the user, which may open up to provide access for the user's head. By way of non-limiting example, each front portion 20 has a right portion and a left portion having hinge joint 22 on its one end connecting the head and neck restrainer, and locking device 24 on its other end for buckling up the right portion and the left portion in the middle of the front portion.

Alternatively, each of front portions 20 may be a single portion containing a hinge joint on one end connecting the head and neck restrainer, and a locking device on its other end for buckling up with head and neck restrainer 10.

The inner surface of the head and neck restrainer is covered by a shock absorbing layer 26 for protecting the user's face and head during impact. Alternatively, the head and neck restrainer may be in other form, such as a conventional helmet.

Figure 4:
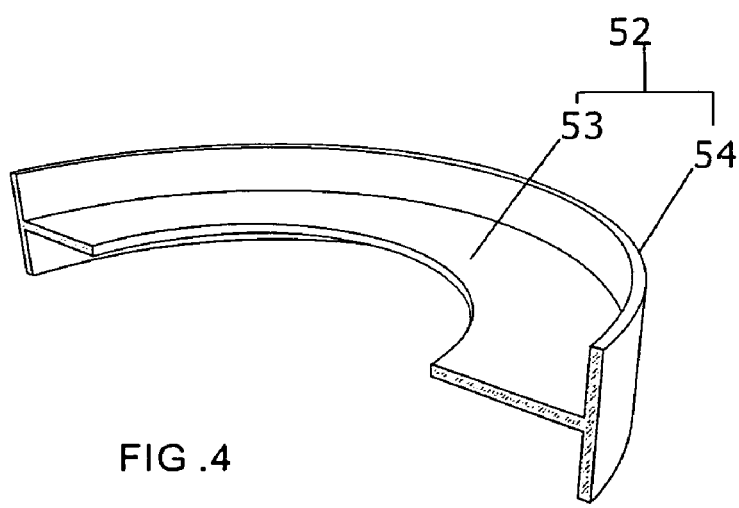
FIG. 4 is a perspective partial view of a T-shaped rail used with the apparatus of FIG. 2.

As illustrated in FIGS. 3A and 4, a portion of joint device 50 (see FIG. 6) includes metal curvilinear T-shaped rail 52 protruding out from and extending around the back portion of head and neck restrainer 10. The T-shaped rail has a curvilinear horizontal plane 53 attached to outer shell 12. By way of example, the horizontal plane may be about 5 cm wide and about 5 mm thick. The horizontal plane extends from a position on one side of the outer shell behind front opening 16 around the back portion of the head and neck restrainer to the corresponding position on the other side. Horizontal plane 53 is further attached to a curvilinear vertical plane 54 having the same length as the horizontal plane. By way of example, the vertical plane may be about 6 cm high and about 5 mm thick.

As illustrated in FIGS. 3A and 3B, a lower front portion 21 of the head and neck restrainer 10 is provided for supporting the user's chin during a sudden forward movement of the head. Some of the restraining force from the joint device 50 can therefore be transmitted to a lower position of the head, that is, the chin area near the upper part of the neck of the user. Otherwise, the restraining force will be focused on the forehead of the user and may cause injury to the user's neck when the sudden forward movement of the head is restrained.

Figure 5B:
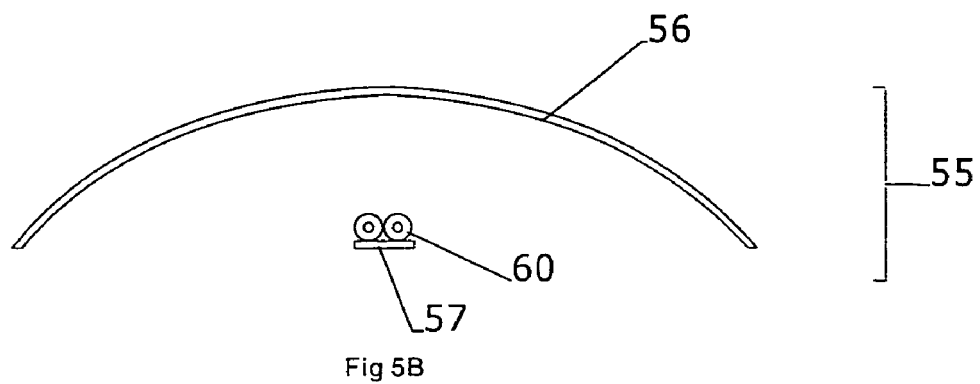
FIG. 5B is a cross-sectional view of the curved metal case, taken along line 5B-5B of FIG. 5A.
Figure 5A:
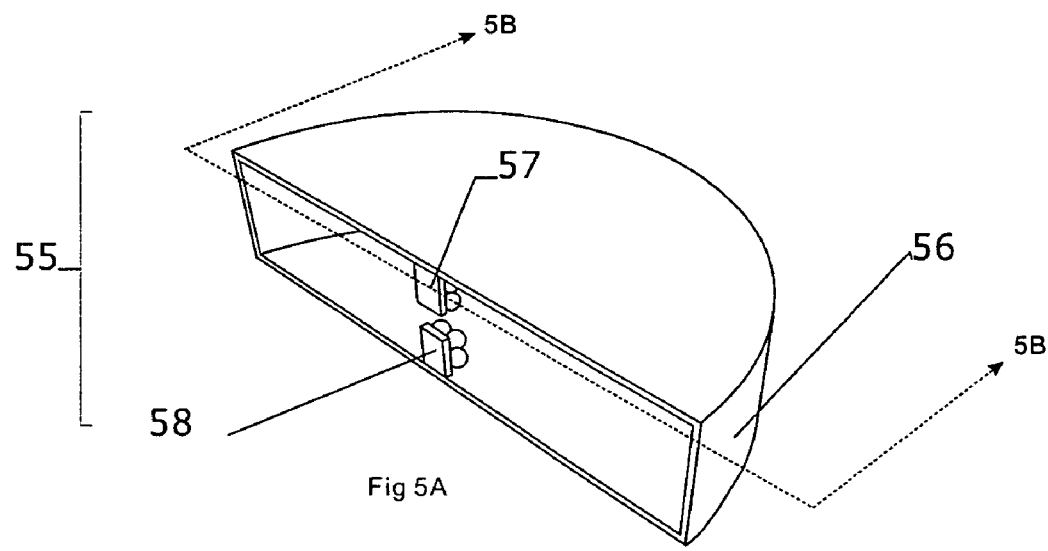
FIG. 5A is a perspective view of a curved metal case used with the apparatus of FIG. 2.

As illustrated in FIGS. 5A and 5B, another portion of joint device 50 includes curved metal case 55 having a back wall 56 in the shape of the vertical plane 54 of T-shaped rail 52 for receiving the T-shaped rail. Two clamp teeth 57 and 58 are formed at the front of the curved metal case extending from the top and bottom inner surface of the curved metal case near the middle part to interlock with the T-shaped rail 52.

Figure 6:
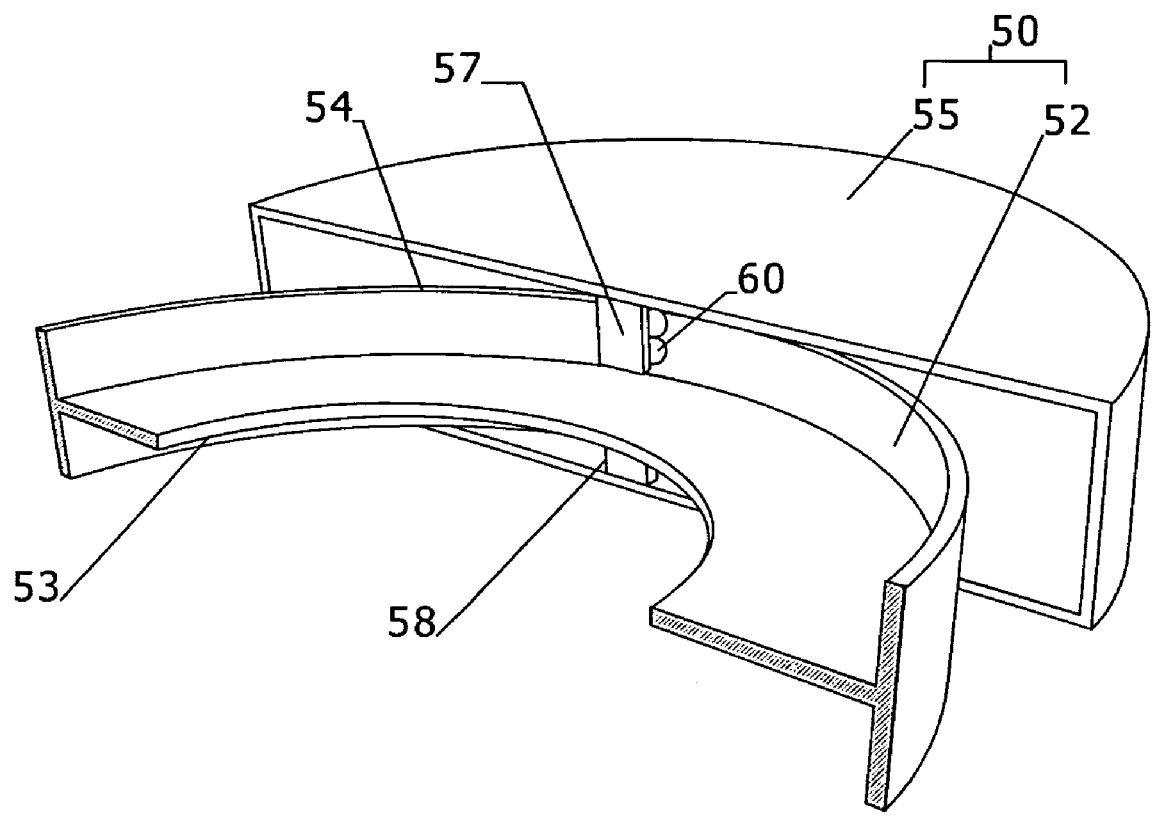
FIG. 6 is a perspective partial view of the structures of FIGS. 4 and 5 in an interlock position for use in accordance with an embodiment of the present invention.

The interlocked position of the T-shaped rail 52 and the curved metal case 55, forming joint device 50, is illustrated in FIG. 6. The clamp teeth 57 and 58 are in a curvilinear shape to match with the vertical plane of the T-shaped rail. The curved metal case further contains bearings 60 adjacent to the clamp teeth and above and below the T-shaped rail for reducing friction encountered in the sliding movement of the T-shaped rail inside the curved metal case near the clamp teeth and for enhancing a smooth turning movement of the head and neck restrainer 10 with respect to the joint device 50. By way of non-limiting example, the inner dimension of the curved metal case may be about 8 cm high and about 5.5 cm deep in the middle part.

Bearings 60 may be ball bearings or cylindrical bearings arranged in a plane parallel with curvilinear vertical plane 54 of T-shaped rail 52. The bearings are positioned anterior to vertical plane 54. All bearings are in contact with the vertical plane when the vertical plane is in touch with the bearings vertically.

Figure 7:
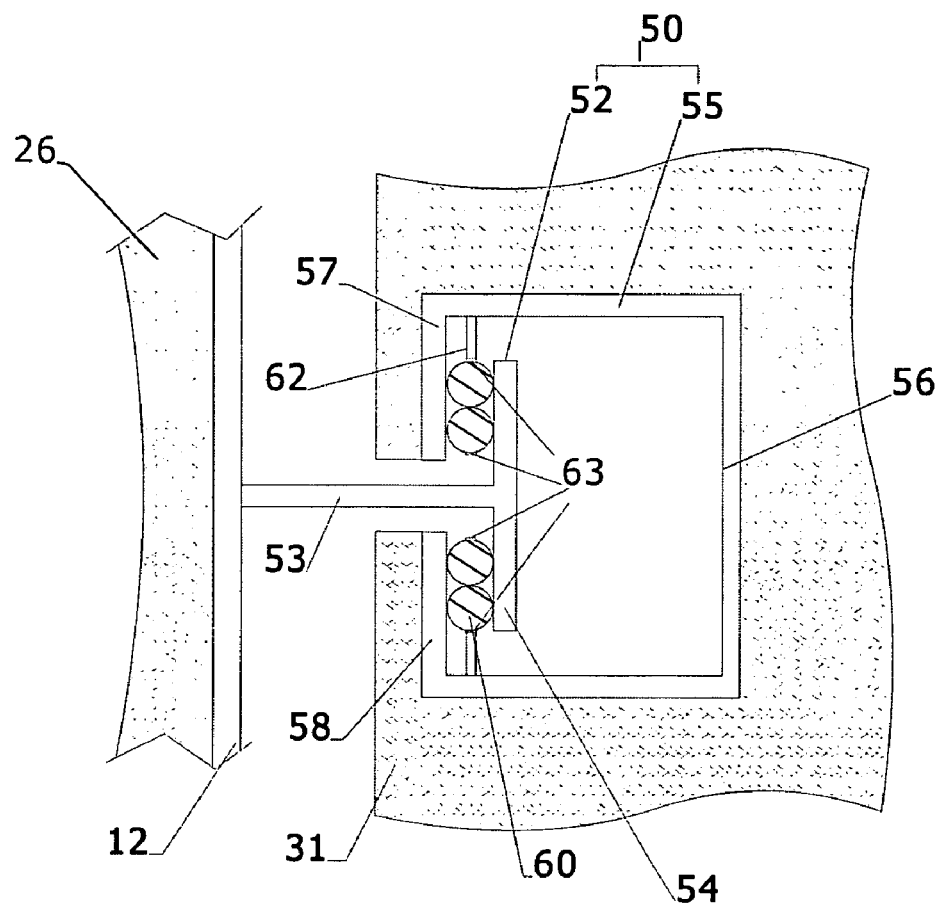
FIG. 7 is a enlarged partial sectional view of the structure of FIG. 6.

By way of non-limiting example, curved metal case 55 contains eight ball bearings of about 1 cm diameter each. As illustrated in FIG. 7, four bearings in two vertical columns are positioned above horizontal plane 53 and anterior to curvilinear vertical plane 54. Two vertical poles 62 may be attached to the inner top surface of the curved metal case adjacent to upper clamp tooth 57 for co-axially connecting the bearings in each vertical column and for fixing the axial turning direction of the bearings. Two circular stops 63 may be formed on each pole for fixing the position of the bearings to the non-attached end of the pole. By way of example, each pole has a length of about 3 cm.

By way of non-limiting example, four bearings 60 and two vertical poles 62 are arranged in the curved metal case 55 below horizontal plane 53 of T-shaped rail 52 and in their corresponding positions of the bearings and the poles above the horizontal plane.

By way of example, there may be approximately 2 cm vertical distance between top and bottom bearings 60. The front of clamp teeth 57 and 58 may be covered by cushioning material 31 of about 1 cm thick. In the position when vertical plane 54 is in touch vertically with all eight bearings 60, by way of example, there may be approximately 2.5 cm horizontal distance between the surface curvature of outer shell 12 and the corresponding cushioning material in front of the clamp teeth. In the same position, there may be an approximately 4 cm horizontal distance between vertical plane 54 and back wall 56 of curved metal case 55 wherein T-shaped rail 52 may tilt upward or downward in a limited degree. The user is thus allowed to move their head in a degree within a safe range, for example, of about 2.5 cm forward and backward and about 2 cm upward and downward, but is restrained from extensive backward and forward movement of the neck which may cause whiplash. The user can turn their head freely to the right and left.

As illustrated in FIGS. 8A, 8B and 8C, curved metal case 55 is embedded in cavity 66 in the shape of the curved metal case in the front portion of shock absorber 30. Clamp teeth 57 and 58 may be covered by cushioning material 31 of the shock absorber at its front for absorbing the shock from the impact of outer shell 12. As illustrated in FIGS. 3A and 3B, the back of the outer shell may be in the form of a curvilinear vertical plane having a height greater than the height of the curved metal case, so that the contact area for absorbing the shock from an impact between the front of clamp teeth 57 and 58 and outer shell is maximized.

Shock absorber 30 may include solely cushion 32 of collapsible material formed from, for example, a foamed polymeric material for absorbing the shock of impact from outer shell 12. Front surface 34 of the cushion is shaped to fit the head and neck restrainer 10 while back surface 36 of the cushion is of a curved shape for matching with seat back 46. The shock absorber absorbs the shock from behind when the vehicle collision occurs at the back, and prevents the shock from being transmitted directly to the user. H-shaped opening 35 is formed on the front surface of the cushion for the access of T-shaped rail 52.

Figure 9:
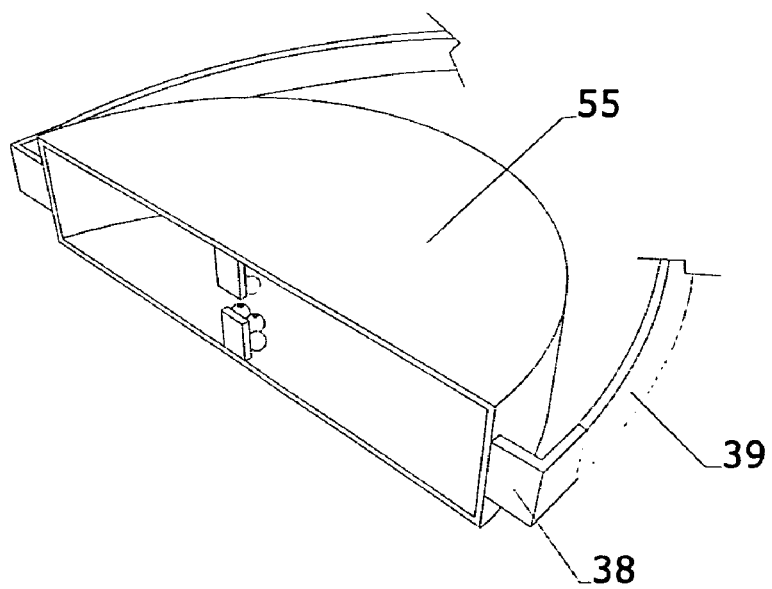
FIG. 9 is a perspective view of the device of FIG. 5A in an attached condition.
Figure 10:
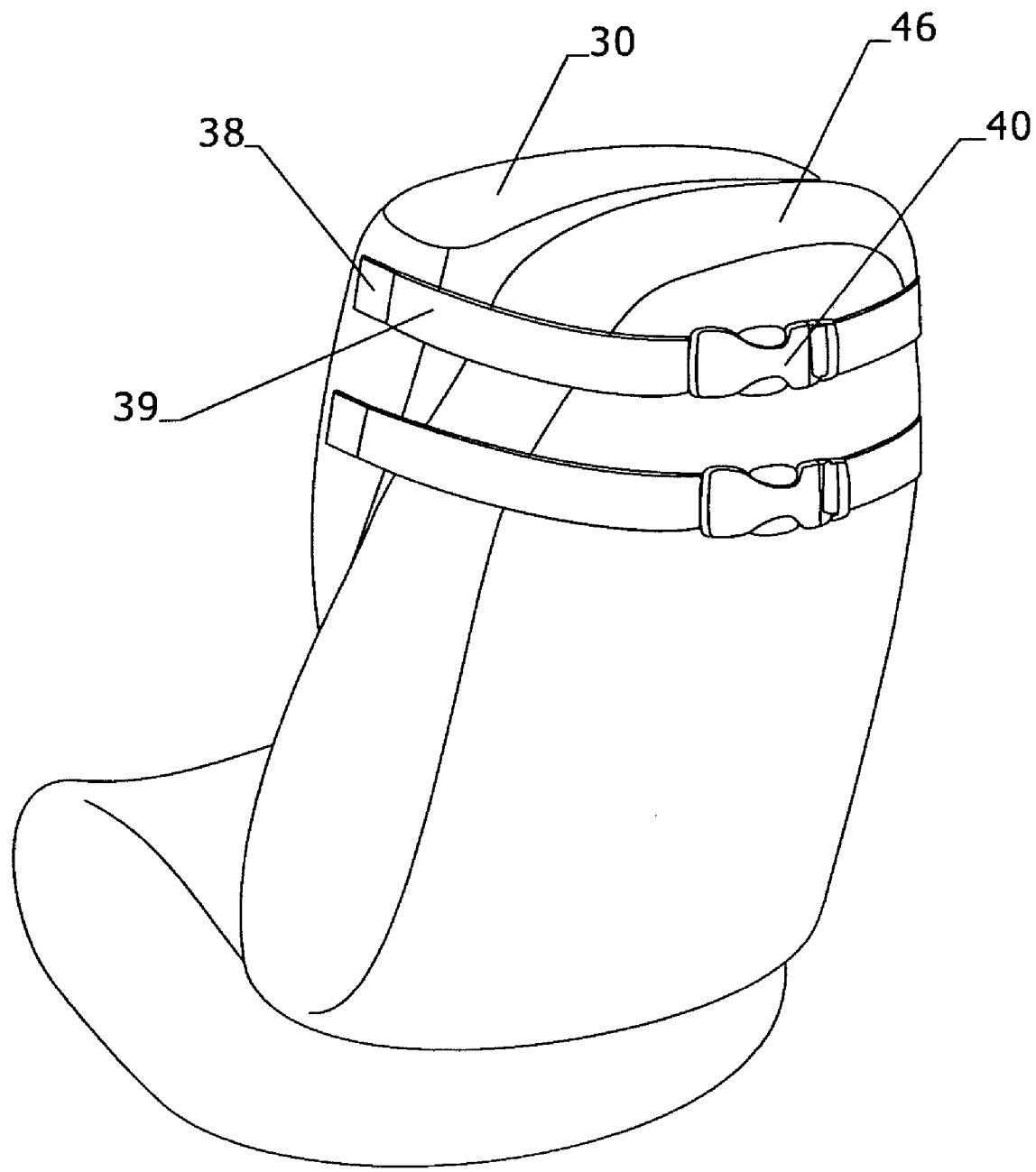
FIG. 10 is a rear perspective view of the apparatus of FIG. 8.

As illustrated in FIGS. 8C, 9 and 10, the shock absorber 30 further includes two metallic strips 38 each extending horizontally and sideward from ends of back wall 56 of curved metal case 55. A portion of said metallic strip is contained inside cushion 32. The metallic strip may further extend backward at the side of the shock absorber and connect with length adjustable strap 39 extending backward along side of the shock absorber for securing the shock absorber onto seat back 46. Straps 39 further include buckle device 40 for connection behind the seat back 46 for securing the shock absorber onto the seat back. The shock absorber may further contain, another set of straps and buckle device at a position lower than strap 39 for securing shock absorber 30 onto the seat back.

Figure 11:
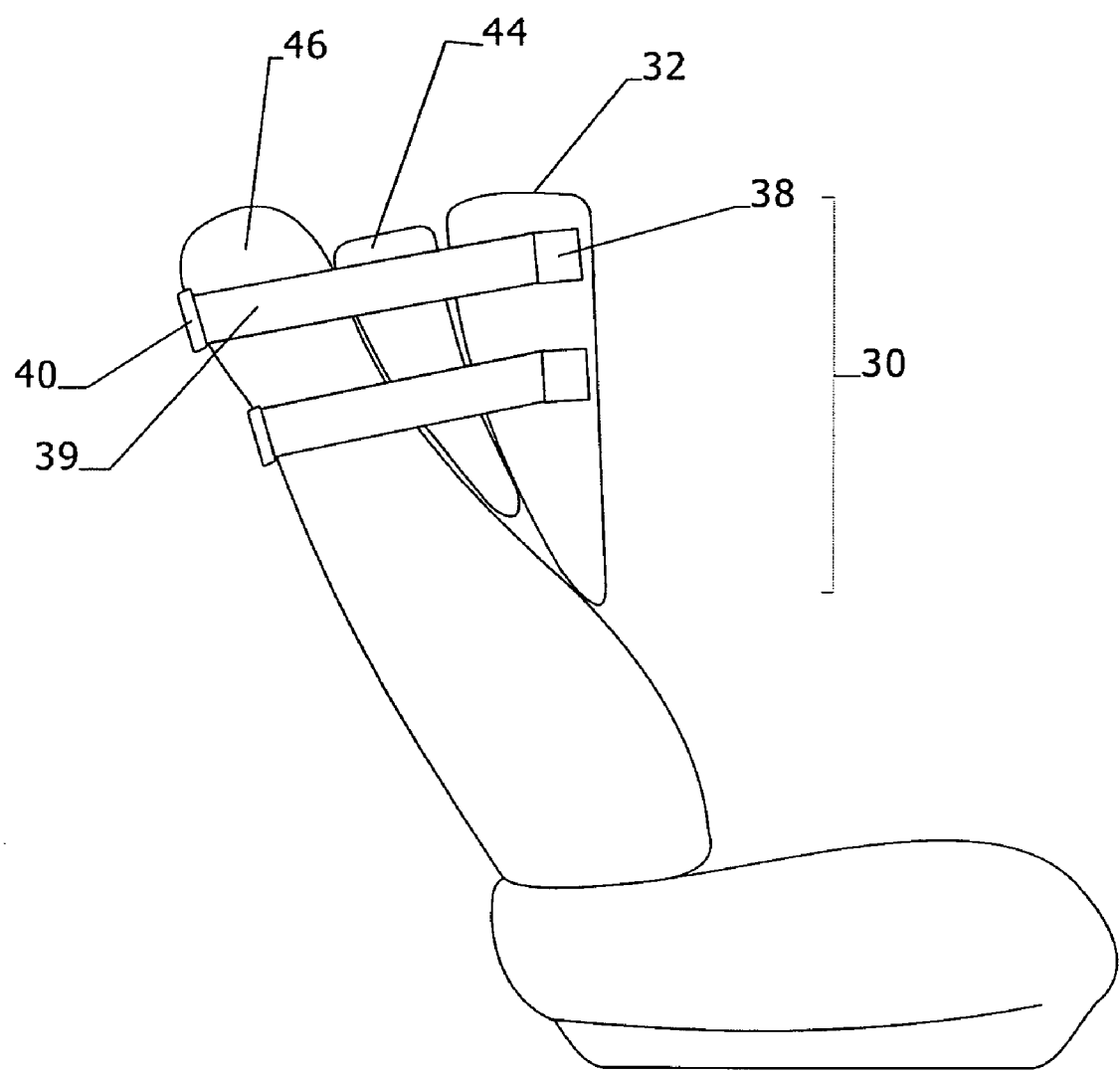
FIG. 11 is a side view of the apparatus of FIG. 8 showing an additional cushion sheet.

As illustrated in FIG. 11, additional cushion sheet 44 of various thickness, or numerous cushion sheets, may be placed between cushion 32 and seat back 46 for adjusting the thickness of shock absorber 30 to fit with the user's head and neck. The front and back surfaces of the cushion sheet are adapted to match with the shape of the surfaces of the cushion and the seat back or with each other.

As an alternative, shock absorber 30 may be directly built into a seat back to be sold with the vehicle.

Figure 12:
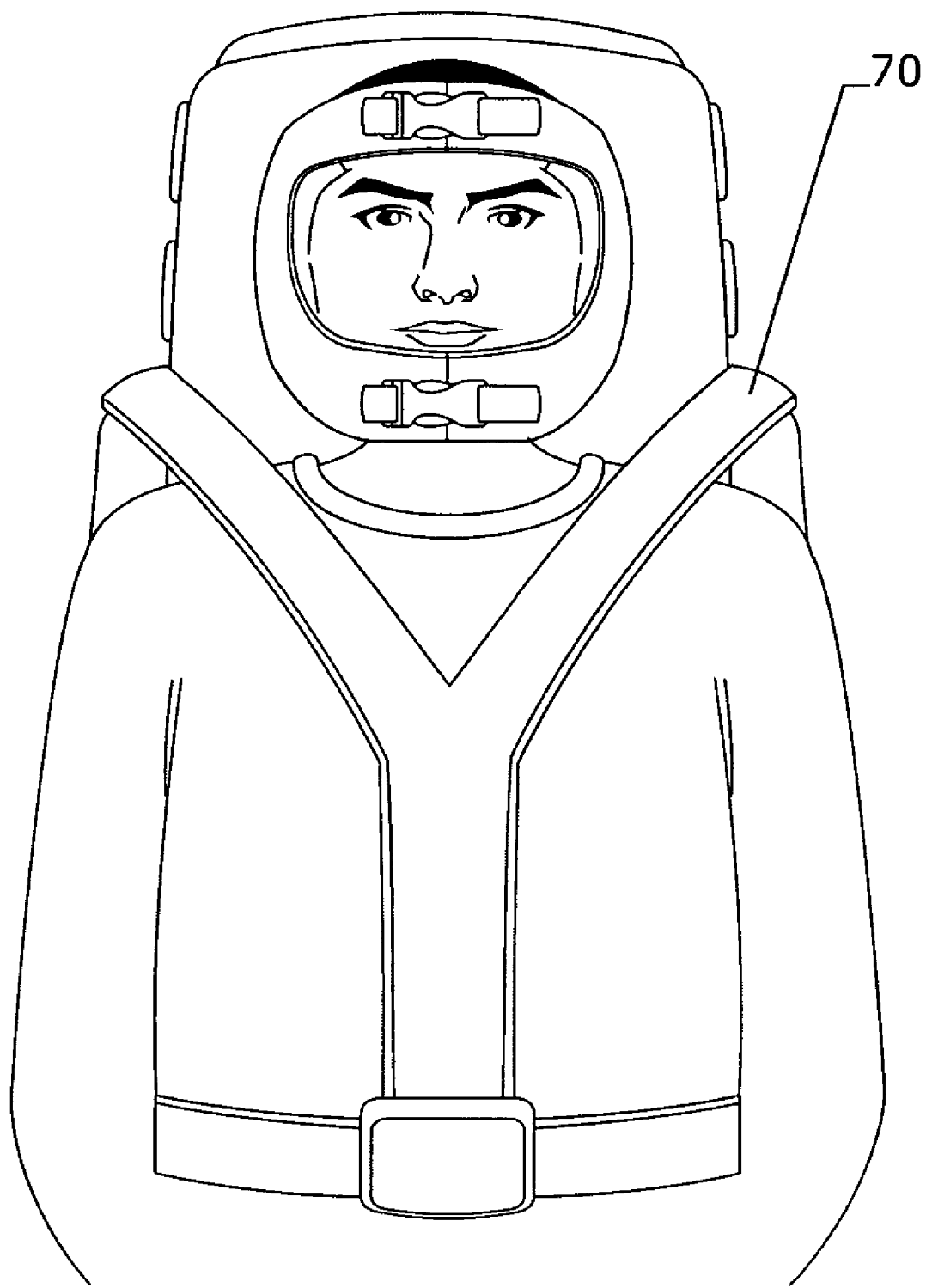
FIG. 12 is the front view of the whiplash restrainer in accordance with an embodiment of the present invention in use.

As illustrated in FIG. 12, the present invention should be used with body restraining device 70 attached to seat back 46, such as a safety belt, to restrain the body of the user on to the seat back. By way of unlimited example, the safety belt is bilateral to spread the force evenly on the user's body.

While the invention has been described in detail with reference to disclosed embodiments, various modifications within the scope of the invention will be apparent to those of ordinary skill in this technological field. It is to be appreciated that features described with respect to one embodiment typically may be applied to other embodiments. Therefore, the invention properly is to be construed only with reference to the claims.

What is claimed is:

1. A whiplash restrainer to be used in a vehicle with a body restraining device in conjunction with a seat having a seatback, the whiplash restrainer comprising:
   a head and neck restrainer comprising a stiff helmet having a back portion, an outer surface and an inner surface covered by an elastic cushioning material;
   a shock absorber having a body of elastic cushioning material being shaped and configured for attaching with the front surface of said seat back, and a front surface; and
   a joint device configured to connect said head and neck restrainer with said shock absorber, wherein a cavity is formed in the front surface of said shock absorber shaped and configured for containing and engaging said joint device.

2. The whiplash restrainer according to claim 1, wherein said joint device further comprises:
   a T-shaped curvilinear rail protruding out from the back portion of said head and neck restrainer and extending parallel and exterior to said outer surface;
   a curved case receiving said T-shaped curvilinear rail, said curved case comprising a curvilinear back wall, a top plate, and a bottom plate, which together form a rectangular opening, said curved case having a middle portion extending vertically from each said top plate and said bottom plate at said opening, said opening being provided adjacent said front surface of said shock absorber, said middle portions interlocking with said T-shaped curvilinear rail wherein said curved case is disposed in the cavity of said shock absorber.

3. The whiplash restrainer according to claim 2, wherein said T-shaped curvilinear rail further comprises:
   a horizontal curvilinear plane attached to said outer surface of said head and neck restrainer; and
   a vertical curvilinear plane attached to and perpendicular to said horizontal curvilinear plane.

4. The whiplash restrainer according to claim 3, wherein said curved case further comprises a plurality of bearings disposed above and below said horizontal curvilinear plane and anterior to said vertical curvilinear plane.

5. The whiplash restrainer according to claim 4, wherein said curved case further comprises:
   a plurality of poles each attached to said top plate of said curved case at one end and adjacent to said middle portion of said curved case, co-axially connecting a plurality of said bearings; and a plurality of poles each attached to said bottom plate of said curved case at one end and adjacent to said middle portion of said curved case, co-axially connecting a plurality of said bearings.

6. The whiplash restrainer according to claim 2, wherein said head and neck restrainer further comprises:
   at least one front portion which can be moved between an open position and a closed position for fitting in the user's head;
   at least one hinge joint for connecting said front portion to said head and neck restrainer; and
   a locking device for locking said front portion in the closed position.

7. The whiplash restrainer according to claim 2, wherein said head and neck restrainer further comprises an open top portion for exposing the top of the user's head for ventilation.

8. The whiplash restrainer according to claim 6, wherein said head and neck restrainer further comprises an open top portion for exposing the top of the user's head for ventilation.

9. The whiplash restrainer according to claim 2, wherein said head and neck restrainer further comprises an open front portion for exposing the user's face for ventilation.

10. The whiplash restrainer according to claim 6, wherein said head and neck restrainer further comprises an open front portion for exposing the user's face for ventilation.

11. The whiplash restrainer according to claim 2, wherein said back portion of said head and neck restrainer is in the form of a curvilinear vertical plane.

12. The whiplash restrainer according to claim 6, wherein said back portion of said head and neck restrainer is in the form of a curvilinear vertical plane.

13. The whiplash restrainer according to claim 2, wherein said shock absorber further comprises:
   a stiff strip extending from each side of said curved case; and
   a length adjustable strap having a distal end, and a proximal end attached to said strip at the side of said shock absorber.

14. The whiplash restrainer according to claim 3, wherein said shock absorber further comprises:
   a stiff strip extending from each side of said curved case; and
   a length adjustable strap having a distal end, and a proximal end attached to said strip at the side of said shock absorber.

15. The whiplash restrainer according to claim 4, wherein said shock absorber further comprises:
   a stiff strip extending from each side of said curved case; and
   a length adjustable strap having a distal end, and a proximal end attached to said strip at the side of said shock absorber.

16. The whiplash restrainer according to claim 13, wherein said length adjustable strap further comprises a locking device at said distal end for securing said shock absorber onto the seat back.

17. The whiplash restrainer according to claim 15, wherein said length adjustable strap further comprises a locking device at said distal end for securing said shock absorber onto the seat back.

18. The whiplash restrainer according to claim 2, and further comprising at least one cushion sheet shaped and configured to be disposed between said shock absorber and the seat back.

19. The whiplash restrainer according to claim 5, and further comprising at least one cushion sheet shaped and configured to be disposed between said shock absorber and said seat back.

20. The whiplash restrainer according to claim 2, wherein said head and neck restrainer is built into said seat back.

21. The whiplash restrainer according to claim 5, wherein said head and neck restrainer is built into said seat back.

22. The whiplash restrainer according to claim 5, wherein said middle portion of said curved case is shaped curvilinear to match with the said vertical plane of said T-shaped rail.

23. The whiplash restrainer according to claim 4, wherein said bearings are ball bearings.

24. The whiplash restrainer according to claim 5, wherein each said pole further comprises a plurality of stops attached to said pole for fixing said bearings on the non-attached end of said pole.

25. The whiplash restrainer according to claim 5, wherein said head and neck restrainer further comprises:
   at least one front portion which can be moved between an open position and a closed position for fitting in the user's head;
   at least one hinge joint for connecting said front portion to said head and neck restrainer; and
   a locking device for locking said front portion in the closed position.

26. The whiplash restrainer according to claim 5, wherein said head and neck restrainer further comprises an open top portion for exposing the top of the user's head for ventilation.

27. The whiplash restrainer according to claim 5, wherein said head and neck restrainer further comprises an open front portion for exposing the user's face for ventilation.

28. The whiplash restrainer according to claim 1, wherein said head and neck restrainer further comprises a lower front portion for supporting the user's chin in a sudden forward movement of the head, whereby part of the restraining force from said joint device is transmitted to the chin near the upper part of the neck of the user.

29. A whiplash restrainer to be used in a vehicle with a body restraining device in conjunction with a seat having a seatback, the whiplash restrainer comprising:
   a head and neck restrainer comprising a stiff helmet having a back portion, an outer surface and an inner surface covered by an elastic cushioning material, and a lower front portion for supporting the user's chin in a sudden forward movement of the head;
   a shock absorber having a body of elastic cushioning material being shaped and configured for attaching with the front surface of said seat back, a front surface and, and a cavity formed on said front surface;
   a T-shaped curvilinear rail protruding out from the back portion of said head and neck restrainer and extending parallel and exterior to said outer surface;
   a curved case receiving said T-shaped curvilinear rail, said curved case comprising a curvilinear back wall, a top plate, and a bottom plate, which together form a rectangular opening, said curved case having a middle portion extending vertically from each said top plate and said bottom plate at said opening, said opening being provided adjacent said front surface of said shock absorber, said middle portions interlocking with said T-shaped curvilinear rail, wherein said curved case is disposed in the cavity of said shock absorber, said cavity is shaped and configured for containing and engaging said curved case.

* * * * *